(12) United States Patent
Min et al.

(10) Patent No.: US 9,095,717 B2
(45) Date of Patent: Aug. 4, 2015

(54) METHODS AND SYSTEMS FOR ANALYZING VALVE RELATED TIMING AND MONITORING HEART FAILURE

(71) Applicant: PACESETTER, INC., Sylmar, CA (US)

(72) Inventors: Xiaoyi Min, Camarillo, CA (US); Rupinder Bharmi, Canyon Country, CA (US); Wenbo Hou, Santa Clarita, CA (US); Edward Karst, Los Angeles, CA (US); Kritika Gupta, San Francisco, CA (US); Risshi Shah, San Jose, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/010,366

(22) Filed: Aug. 26, 2013

(65) Prior Publication Data

US 2015/0057716 A1 Feb. 26, 2015

(51) Int. Cl.
*A61N 1/365* (2006.01)
*A61N 1/39* (2006.01)

(52) U.S. Cl.
CPC ........ *A61N 1/36578* (2013.01); *A61N 1/36521* (2013.01); *A61N 1/36585* (2013.01); *A61N 1/3962* (2013.01); *A61N 1/3987* (2013.01); *A61N 1/365* (2013.01)

(58) Field of Classification Search
USPC ............. 607/5, 8, 9, 11, 25, 18; 600/508–518
See application file for complete search history.

(56) References Cited

U.S. PATENT DOCUMENTS

| 7,689,283 | B1 | 3/2010 | Schecter | |
|---|---|---|---|---|
| 2003/0181952 | A1* | 9/2003 | Jverud et al. | 607/17 |
| 2010/0121398 | A1* | 5/2010 | Bjorling et al. | 607/17 |
| 2010/0152795 | A1* | 6/2010 | Schecter | 607/4 |
| 2010/0152802 | A1* | 6/2010 | Min | 607/14 |
| 2011/0237968 | A1* | 9/2011 | Blomqvist et al. | 600/509 |
| 2013/0079839 | A1* | 3/2013 | Lian et al. | 607/25 |
| 2014/0276125 | A1* | 9/2014 | Hou et al. | 600/483 |

* cited by examiner

*Primary Examiner* — Allen Porter, Jr.

(57) ABSTRACT

A method and system are provided to analyze valve related timing and monitor heart failure. The method and system comprise collecting cardiac signals associated with an atrial chamber of interest; collecting dynamic impedance (DI) data along an atria-function focused (AFF) vector to form a DI data set, the DI data set including information corresponding to a mechanical function (MF) of a valve associated with the atrial chamber of interest; identifying, from the cardiac signals, an intra-atrial conduction timing (IACT) associated with the atrial chamber of interest; estimating an MF landmark at which the mechanical function of the valve occurs based on the DI data set; analyzing a timing delay between the MF landmark and the IACT; and adjusting a therapy, based on the timing delay, to encourage atrial contribution to ventricular filling.

20 Claims, 4 Drawing Sheets

METHODS AND SYSTEMS FOR ANALYZING VALVE RELATED TIMING AND MONITORING HEART FAILURE

BACKGROUND OF THE INVENTION

Embodiments of the present invention generally relate to characterizing cardiac function, and more particularly to methods and systems that analyze valve related timing and monitor heart failure.

Today, pacemaker configuration is often performed by selecting a desired lead location for a specific patient (e.g., apical vs septal) and then programming the parameters of the pacemaker, such as the AV and/or VV delay, the rate responsive AV and/or VV delay and the like. Today, cardiac resynchronization therapy (CRT) configuration is similarly performed by selecting a desired lead location (e.g., by avoiding infarct zones, reduced dyssynchrony, LV apical vs septal) and then programming the CRT device with desired AV and VV delays. The AV and VV delays are selected traditionally by physicians through the use of an echocardiography evaluation method. However, the echocardiography evaluation method is time consuming and has high variations.

In addition, device manufacturers have implemented algorithms within implanted medical devices that select AV and VV delays based on intra-cardiac electrograms (IEGM). For example, one device-based method uses P-wave duration to estimate intra-atrial conduction time (IACT) for setting the timing of ventricular (V) pacing. This device-based method is intended to achieve similar effects as an echocardiography evaluation based method. However, device-based methods that utilize the P-wave, as detected in the RA, represent a rough estimation of IACT. As such, the potential exists that the P-wave estimate may be an inaccurate estimate of IACT.

Device manufacturers have also implemented algorithm within implanted medical devices to detect heart failure (HF). HF is not a condition in which the heart abruptly stops beating. Instead, HF refers to a dysfunction in which the myocardial tissue fails to contract or relax properly.

Furthermore, it is preferred to tailor each device to the individual patient's underlying etiology and functional status. Yet, a comprehensive echocardiography evaluation assessment is time consuming and has high variations. Also, when the parameters of a pacemaker are set to a preferred setting, while a patient is in the clinic, the same parameter settings may not reflect the best parameter settings for the patient when the person is ambulatory and active. Thus a need exists for further improving AV delay algorithms.

SUMMARY

In accordance with embodiments herein, a method is provided to analyze valve related timing and monitor heart failure. The method comprises collecting cardiac signals associated with an atrial chamber of interest and collecting dynamic impedance (DI) data along an atria-function focused (AFF) vector to form a DI data set. The DI data set includes information corresponding to a mechanical function (MF) of a valve associated with the atrial chamber of interest. The method then identifies, from the cardiac signals, an intra-atrial conduction timing (IACT) associated with the atrial chamber of interest. The method then estimates an MF landmark at which the mechanical function of the valve occurs based on the DI data set. The method then analyzes a timing delay between the MF landmark and the IACT and adjusts a therapy, based on the timing delay, to encourage atrial contribution to ventricular filling.

Optionally, the method may collect DI data utilizing an IMD case electrode and at least one of an SVC electrode or an RA electrode to define the AFF vector and to collect the DI data. As another option, the method may identify a feature of interest (FOI) in a P-wave representing the end of the IACT. Optionally, the method may be further configured to determine, as the time delay, an interval between the FOI in the P-wave and the MF landmark. Optionally, the estimating operation may include estimating the MF landmark by determining a timing of an impedance waveform peak associated with the DI data set. As another option, the first chamber may represent the right atrium and the MF landmark may represent an estimate for one of mitral valve closure (MVC) or mitral valve opening (MVO).

Optionally, the method may analyze at least one morphologic characteristic of the DI data set to estimate the MF landmark. Optionally, the method may further identify a second timing delay between a peak of a QRS complex from the cardiac signals and the MF landmark, wherein the MF landmark represents opening of an aortic valve, and utilizes the timing delay to monitor progression of heart failure. As yet another option, the method may identify, from a P-wave, a time between right atrial and left atrial activation, in a single cycle, the total duration constituting the IACT. As yet another option, the method may estimate the MF landmark by determining, as a morphologic characteristic, at least one of i) a peak, or ii) a maximum negative change per unit time (dZ/dt) of the DI data. As another option, the method may further comprise monitoring the timing delay for progression of heart failure.

In accordance with an embodiment, a system is provided for characterizing and analyzing valve-related mechanical timing. The system comprises inputs configured to collect cardiac signals associated with an atrial chamber of interest; and a dynamic impedance (DI) module configured to collect dynamic impedance data along an atria-function focused (AFF) vector to form a DI data set. The DI data set includes information corresponding to a mechanical function (MF) of a valve associated with the atrial chamber of interest. The system also includes a cardiac signals (CS) module configured to identify, from the cardiac signals, an intra-atrial conduction timing (IACT) associated with the atrial chamber of interest. The system also includes an MF landmark module configured to estimate an MF landmark at which the mechanical function of the valve occurs based on the DI data set. The system also includes an analysis module configured to analyze a timing delay between the MF landmark and the IACT. The system also includes a therapy module configured to adjust a therapy, based on the timing delay, to encourage atrial contribution to ventricular filling.

Optionally, the CS module may be further configured to identify a feature of interest (FOI) in a P-wave representing the end of the IACT.

Optionally, the inputs may be further configured to collect DI data includes utilizing an IMD case electrode and at least one of an SVC electrode and an RA electrode to define the AFF vector and to collect the DI data.

Optionally, the MF landmark module may be further configured to estimate the MF landmark by determining a timing of an impedance waveform peak associated with the DI data set. Optionally, the MF landmark module may be further configured to estimate one of mitral valve closure (MVC) or mitral valve opening (MVO) in the right atrium. As another option, the MF landmark module may be further configured to determine, as a morphologic characteristic, at least one of i) a peak, or ii) a maximum negative change per unit time (dZ/dt) of the DI data.

Optionally, the analysis module may be further configured to analyze at least one morphologic characteristic of the DI data set to estimate the MF landmark. Optionally, the analysis module may be further configured to identify a second timing delay between a peak of a QRS complex from the cardiac signals and the MF landmark, wherein the MF landmark represents opening of an aortic valve, and utilizing the timing delay to monitor progression of heart failure. As yet another option, the analysis module may be further configured to determine, as the time delay, an interval between the FOI in the P-wave and the MF landmark. As another option, the analysis module may be further configured to determine, from a P-wave, a time between right atrial and left atrial activation in a single cycle, the total duration constituting the IACT. Optionally, the analysis module may be further configured to monitor the timing delay for progression of heart failure.

Optionally, the system may further comprise a therapy module configured to change an AV delay of the therapy when the timing delay is below a threshold.

DETAILED DESCRIPTION

In accordance with embodiments herein, methods and systems are described to characterize the systemic and cardiac function of a patient on a beat-by-beat basis. A series of studies in canines were conducted to characterize the effect of hemodynamics on dynamic impedance as recorded from various anode cathode electrode combinations (using transvenous implanted leads). An analysis of the canine data has helped to provide a means of better identifying intra-atrial conduct time and electromechanical delay to improve AV-VV delay and monitor heart failure.

Embodiments are also described for setting parameters to improve AV and/or VV delay, depending on a patient's specific need. For example, embodiments utilize dynamic impedance (DI) data collected along one or more vectors associated with certain cardiac functions such as an atria-function focused (AFF) vector. For example, an AFF vector may be defined by delivering current (and measuring voltage potential) between an RA tip, coil or ring electrode and an IMD case electrode. Alternatively, an AFF vector may be defined by delivering current between an SVC-coil electrode and an IMD case electrode, while measuring a voltage potential between the same or a different SVC-coil electrode and the case electrode. Specific morphological metrics (e.g., i) a peak, ii) a maximum negative DI change per unit time (dZ/dt)) may be associated with DI data collected along the AFF vector, where the morphological metrics enable the DI data to be used to characterize a status of the patient's atrial function.

In general, each chamber has unique traits. Although the chambers coordinate activities to deliver blood throughout the body, each chamber exhibits specific behavioral features that aid in proper operation. For example, the opening and closing of the mitral valve (MO and MC, respectively) regulate blood flow between the left atrium (LA) and the left ventricle (LV). It may be of interest to monitor the operation of each chamber for a given patient. For example, it may be of interest to monitor the emptying of the RA and or the LA in connection with controlling the AV and/or VV timing of an IMD.

Figure 1:
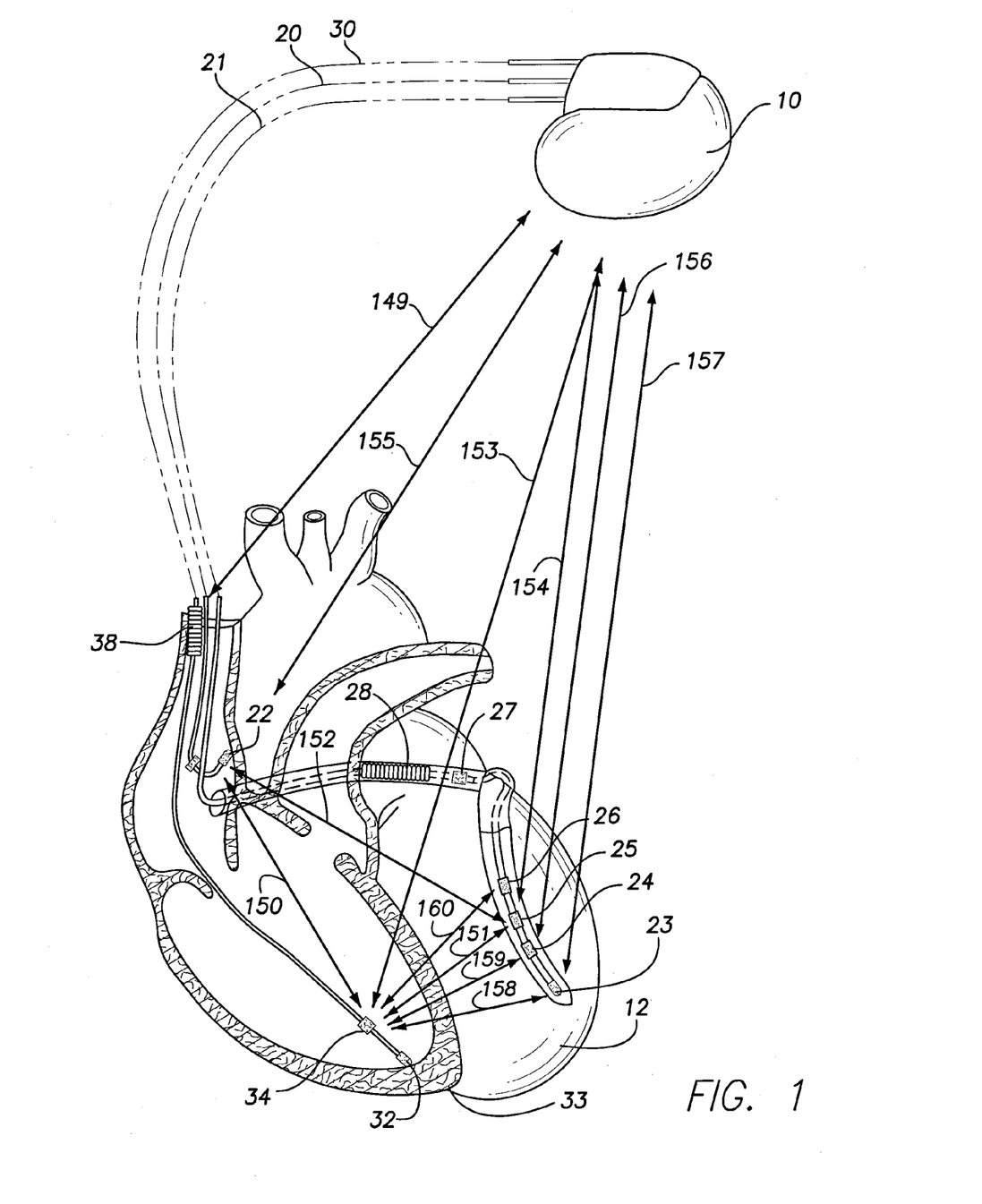
FIG. 1 illustrates a simplified diagram of an implantable medical device in electrical communication with leads implanted in or proximate to a patient's heart in accordance with an embodiment.

FIG. 1 illustrates a simplified diagram of an implantable medical IMD 10 in electrical communication with three leads 20, 21 and 30 implanted in or proximate to a patient's heart 12 for delivering single or multi-chamber stimulation (e.g. pacing, ATP therapy, high voltage shocks and the like) and for characterizing cardiac function according to an embodiment. The stimulation may include pacing pulses that are delivered along one or more pacing vectors. Optionally, the stimulation may include ATP pulses or a high voltage shock that is delivered along one or more ATP therapy vectors, cardioverter vectors or defibrillation vectors. The implantable medical IMD 10 may be a pacing device, a pacing apparatus, a cardiac rhythm management device, an implantable cardiac stimulation device, an implantable cardioverter/defibrillator (ICD), a cardiac resynchronization therapy (CRT) device, a monitoring device and the like. The IMD 10 is programmable, by an operator, to set certain operating parameters, as well as therapy-related parameters. The IMD 10 is configured to operate with various configurations of leads. The IMD 10 is configured to sense various types of information and deliver various types of therapies. For example, the IMD 10 may sense intra-cardiac electrogram signals, impedances and the like.

In FIG. 1, the IMD 10 is coupled to an RA lead 20 having at least an atrial tip electrode 22, which typically is implanted in the patient's right atrial appendage. The IMD 10 is coupled to an LV lead 21 that includes various electrodes, such as an LV tip electrode 23, intermediate LV electrodes 24-26, and LA electrodes 27-28. The LV lead 21 may sense atrial and ventricular cardiac signals and impedances and deliver left ventricular therapy using the LV tip electrode 23, the intermediate LV electrodes 24-26, and the LA electrodes 27 and 28. Left atrial therapy uses, for example, first and second LA electrodes 27 and 28. The LV and LA electrodes 23-28 may be used as sensing sites, where cardiac signals and/or impedances are sensed, and/or may be used as pacing and/or shock therapy sites. A right ventricular lead 30 may include one or more of an RV tip electrode 32, an RV ring electrode 34, and a superior vena cava (SVC) coil electrode 38 (also known as an RA coil electrode). The right ventricular lead 30 is capable of sensing cardiac signals and/or impedances, and delivering stimulation in the form of pacing and shock therapy to the SVC and/or right ventricle.

Optionally, more or fewer electrodes may be utilized. The LV electrodes may be separated further apart or positioned closer to one another. Optionally, all or a portion of the LV electrodes may be shifted along the LV lead 21 until positioned proximate to the mitral valve, aortic valve, or the left atrial ports to/from the pulmonary veins. The LV lead 21 may be inserted directly into the LV chamber or inserted into a vein or artery extending along the heart wall proximate to the left ventricle. Optionally, the LV lead 21 may be coupled to a patch or mesh net electrode that is secured to or located adjacent to an exterior wall of the left ventricle and/or the left atrium.

Embodiments are described herein, whereby multiple electrodes are utilized to sense impedance along multiple sensing vectors in order to measure local impedance information along the select sensing vectors. Impedance measurements collected along the select sensing vectors are utilized to derive dynamic impedance data correlated to one or more cardiac functions.

The IMD 10 defines sensing vectors between various combinations of two or more electrodes 22-28, 32, 34 and 38, and the housing of the IMD 10. FIG. 1 illustrates examples of sensing vectors 149-160. The IMD 10 obtains one or more impedance measurements along the select one or more sensing vectors 149-160 which extend through a select or substantial majority of the portion of the heart or vessels of interest. An individual measured impedance represents the impedance of the walls of the heart 12, the blood in the heart 12 and any external tissue or muscle through which the corresponding active sensing vector extends.

The sensing vector 149 extends between the SVC coil electrode 38 and the CAN electrode of the IMD 10. The sensing vector 150 extends between the RA electrode 22 and the RV ring electrode 34. The sensing vector 151 extends between the RV ring electrode 34 and the LV electrode 25. The sensing vector 152 extends between the LV electrode 25 and the RA electrode 22. The sensing vector 153 extends between the RV ring electrode 34 and the CAN electrode of the IMD 10. The sensing vector 154 extends between the LV electrode 25 and the CAN electrode. The sensing vector 155 extends between the RA electrode 22 and the CAN. Optionally, alternative and/or additional electrodes may be used to form alternative and/or additional sensing vectors.

Each LV and RV electrode 22-38 represents a potential sensing site and/or therapy site. When functioning as a sensing site, the corresponding LV and/or RV electrode senses signals that are utilized to obtain impedance measurements. The sensing sites differ based on the type of device and type of detection algorithm utilized.

For example, in a CRT-D type device, when utilizing the PE algorithm, the device utilizes sensing vectors that extend between the RV coil electrode and the CAN, and between an LV ring electrode and the CAN. In an ICD type device, when utilizing the PE algorithm, the device utilizes sensing vectors that extend between the RV coil electrode and the CAN and between the RV ring electrode and the CAN. In a CRT-P type device, when utilizing the PE algorithm, the device utilizes sensing vectors that extend between the LV ring electrode and the CAN, between the RA ring electrode and the CAN, and between the RV ring electrode and the CAN. In a pacemaker type device, the device generally utilizes an active sensing vector that extends between the RV ring electrode and the CAN.

The impedance measured along the sensing vectors 149-160 may be expressed in terms of ohms. Alternatively, the impedance may be expressed as an admittance measurement. The admittance may be inversely related to the impedance. The impedance measured along the sensing vectors 149-160 may vary based on a variety of factors, including the amount of fluid in one or more chambers of the heart 12 and/or thoracic space. Blood is more electrically conductive than the myocardium of the heart 12. Consequently, as the amount of blood in the atrium of interest increases, the impedance measured along the active sensing vector decreases. Conversely, the impedance measurement increases as there is less blood in the atrium of interest.

Optionally, impedance measurements along various sensing vectors may be utilized to monitor and characterize pressure and blood flow in other chambers of the heart, such as RA, RV, LA and/or LV pressure and blood flow.

Figure 2:
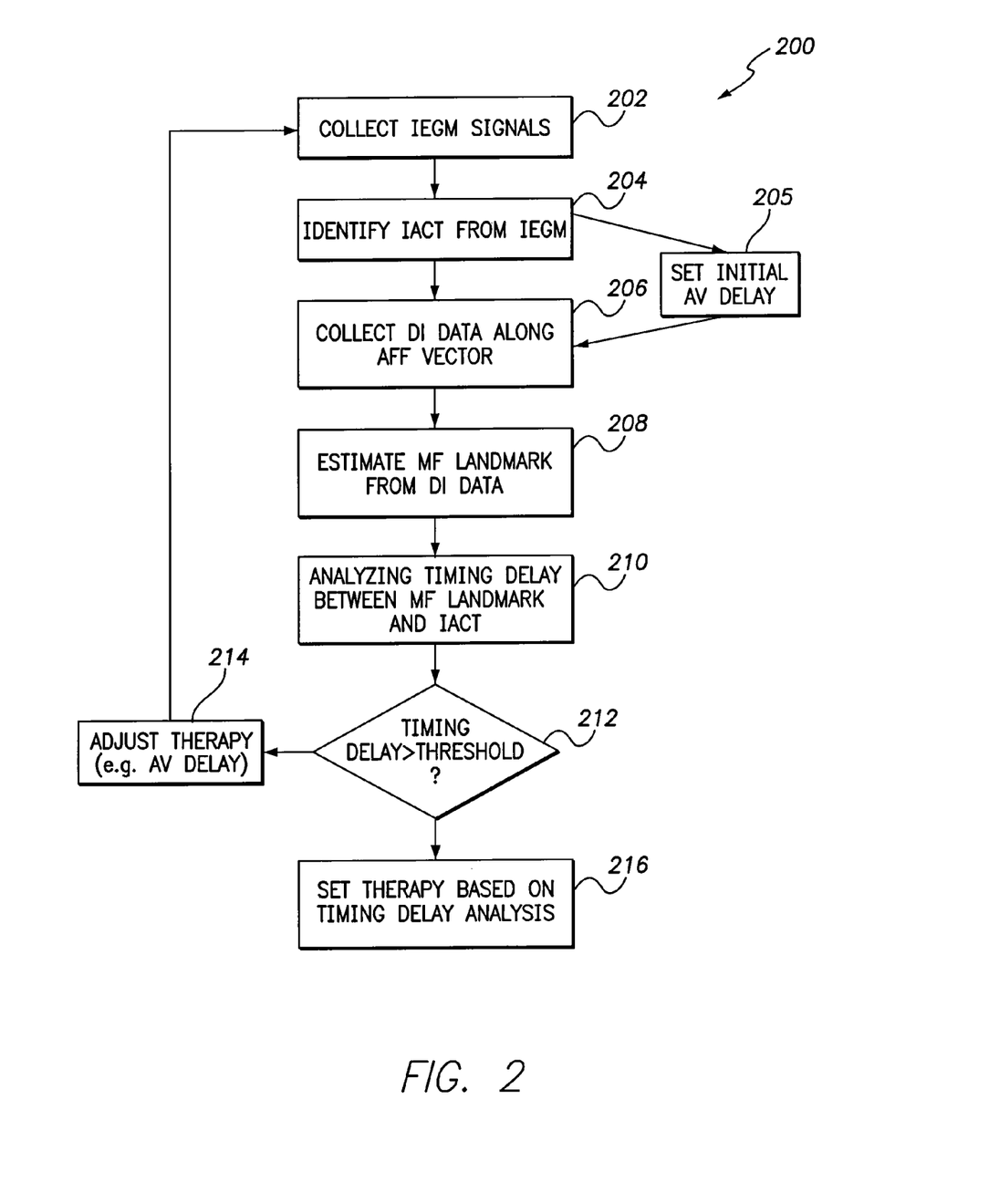
FIG. 2 illustrates a method for analyzing valve related mechanical timing and monitoring heart failure in accordance with an embodiment by one or more of an IMD, external programmer and system described herein.

FIG. 2 illustrates a cardiac function characterization method 200 to be carried out in accordance with an embodiment by one or more of an IMD, external programmer and systems described herein. The method of FIG. 2 begins with the therapy parameters of the IMD 10 set to predetermined values and/or set manually, or automatically by the IMD, based on conventional programming techniques. The IMD therapy parameters may include one or more of AV delay, VV delay, pacing electrode combination, stimulus pulse width, strength, interval, and the like.

Beginning at 202, the method collects cardiac signals associated with electrical and/or mechanical behavior of a heart over at least one cardiac cycle (CC) while an IMD operates based on current IMD therapy parameter values. For example, the cardiac signals may be intra-cardiac electrogram (IEGM) signals, EKG signals, and the like. The cardiac signals may be collected from external skin electrodes, the implanted electrodes 22-38 (along one or more of sensing vectors 149-160) and the like. For example, the IEGM may be sensed by the right atrial lead 20 and the case of the device 10. Alternatively, the IEGMs may be sensed between the SVC coil electrode 38 and the case of the device 10.

At 204, the method identifies an intra-atrial conduction time (IACT) associated with the atrial chamber of interest from the cardiac signals. The IACT represents the time required for electrical signals to propagate to and through the atria. The electrical conduction system of the heart consists of cardiac muscle cells and conducting fibers that are specialized for initiating electrical impulses and conducting the impulses through the heart. The electrical impulses begin in the sinoatrial (SA) node and propagate through the RA, through the Bachmann's bundle, and to the LA.

The IACT represents the electrical conduction time for the depolarization wave front to propagate from the SA to the LA. The IACT may be calculated from the cardiac signals using conventional techniques. As one option, the duration of the IACT may be calculated based on the duration of the P-wave. The duration of the time between the right atrial and left atrial activation, in a single cycle, may constitute the duration of the IACT. For example, the IACT may be calculated based on the time elapsed from the start of the P-wave to the end of the P-wave. Alternatively, the duration of the IACT may be calculated based on the time elapsed from the start of the P-wave to the point when the P-wave reaches a select value (e.g., 20% of the peak). Alternatively, the duration of the IACT may be calculated based on the amount of time the P-wave remains above a threshold (e.g., 15% of the peak value).

The identification at 204 also includes identifying a reference point in time (RPIT) from the IACT. For example, the RPIT may represent a beginning, a center, a peak, or an end of the IACT. The RPIT may be determined by identifying a feature of interest (FOI) from a P-wave. For example, a beginning of the IACT may be determined by identifying, as the FOI, a point at which the P-wave crosses a beginning threshold. As another example, the middle of the IACT may be determined by identifying, as the FOI in the P-wave, the peak of the P-wave. An end of the IACT may be determined by identifying, as the FOI, a point at which the P-wave crosses an ending threshold, or a predetermined time duration following the peak of the P-wave.

Optionally, the RPIT may simply represent the center of the IACT. Optionally, features of interest from other waves (R-wave, T-wave, ST segment, etc.) may be used to identify the duration of the IACT, as well as the reference point in time from the IACT.

The IACT may be calculated from cardiac signals sensed along one sensing vector. Alternatively, the IACT may be calculated from measurements using multiple vectors, where each vector uses at least one different electrode to detect a common event. For example, a vector aligned with RA-case may be used to determine the start of the P-wave and a vector aligned with LA-case may be used to determine the end of the P-wave. The IACT may then be calculated based on the start and end times from the respective vectors as described above. Alternatively, the IACT may be the average IACT calculated individually from each vector using any of the methods described above.

Next, the flow may move to 205. The flow only moves to 205 during the first iteration of the method. During all subsequent iterations, the flow moves from 204 to 206. At 205, the method calculates an initial AV delay. The initial AV delay may be a sum of the IACT identified at 204 and a select time delay δ. For example, the time delay δ may be approximately 30-60 ms. As another example, the AV delay may be 120 ms based on an IACT of 100 ms and a time delay δ of 20 ms. Once the initial AV delay is calculated, the method sets the AV delay equal to the calculated initial AV delay.

Next, at 206, the method collects DI data along an AFF vector to form a DI data set where the DI data set includes, among other things, information corresponding to a mechanical function (MF) of a valve associated with an atrial chamber. For example, the method may collect DI data along an RA-case vector, including sensing an MF of the mitral valve. As another example, the opening or closing of the aortic valve may represent the MF. Optionally, DI data may be collected along multiple AFF vectors.

Current flux density at the surface of the sensing electrode(s) (e.g., SVC or IVC electrode or RA electrode) is relatively high as compared to the current flux density remote from the sensing electrode(s) (e.g., at other chambers of the heart or outside of the heart or at the case electrode). Due to the substantially larger current flux density immediately adjacent the sensing electrode(s), the DI data is primarily affected by changes in the impedance in the area (e.g., the blood) immediately surrounding the sensing electrode(s), while changes in the impedance in areas more remote from the sensing electrode(s) have less relative impact on changes in the dynamic impedance. As an example, the DI data may be recorded from an anode-cathode combination that delivers a reference current between a SVC coil electrode and a case electrode, while measuring voltage between the same or different SVC coil and case electrodes. Hence, when one sensing electrode is in or near the SVC, RA, LA or IVC, the AFF vector detects a DI data stream, a component of which is primarily affected by changes in impedance in the proximal area surrounding the sensing electrode. When the case of the IMD is used as the second sensing electrode, this second sensing electrode is not affected by changes in impedance in the RA or LA.

Optionally, a signal may be obtained that is indicative of patient state (e.g., from an accelerometer), such as the amount of movement (indicative of exercise), the orientation of the patient with respect to gravity (prone, supine, standing, etc.) and the like. Alternatively, the cardiac signal may include information indicative of patient state. The patient state may be analyzed in order to determine when an exertion level or patient orientation is outside of a desirable correlation range. When the patient is undergoing heavy exertion, the DI data may not substantially track certain cardiac functions as closely as desired. Hence, the patient state may be used to determine whether to perform subsequent DI data collection and analysis. For example, when the patient state indicates that the patient is experiencing an excessively high heart rate, the method may determine that impedance measurements will not correlate well to the AFF. Hence, flow may return to 202 and/or the method may determine to cease operation for a period of time or a predetermined number of cardiac cycles. Alternatively, when the patient state indicates that the DI data should correlate to the AFF, then the flow moves to 208.

At 208, the method estimates an MF landmark from the DI data set. The MF landmark represents the time at which an MF of interest occurs within a cardiac cycle. For example, the MF landmark may represent the time at which the mitral valve opens (MVO) or the time at which the mitral valve closes (MVC). As another example, the MF landmark may represent the time at which the aortic valve opens or closes. To estimate the MF landmark, the method analyzes a morphologic characteristic that corresponds to at least one of i) a peak or ii) a maximum negative DI change per unit time (dZ/dt), of the DI data as plotted over a temporal time line for at least one cardiac cycle.

Figure 3:
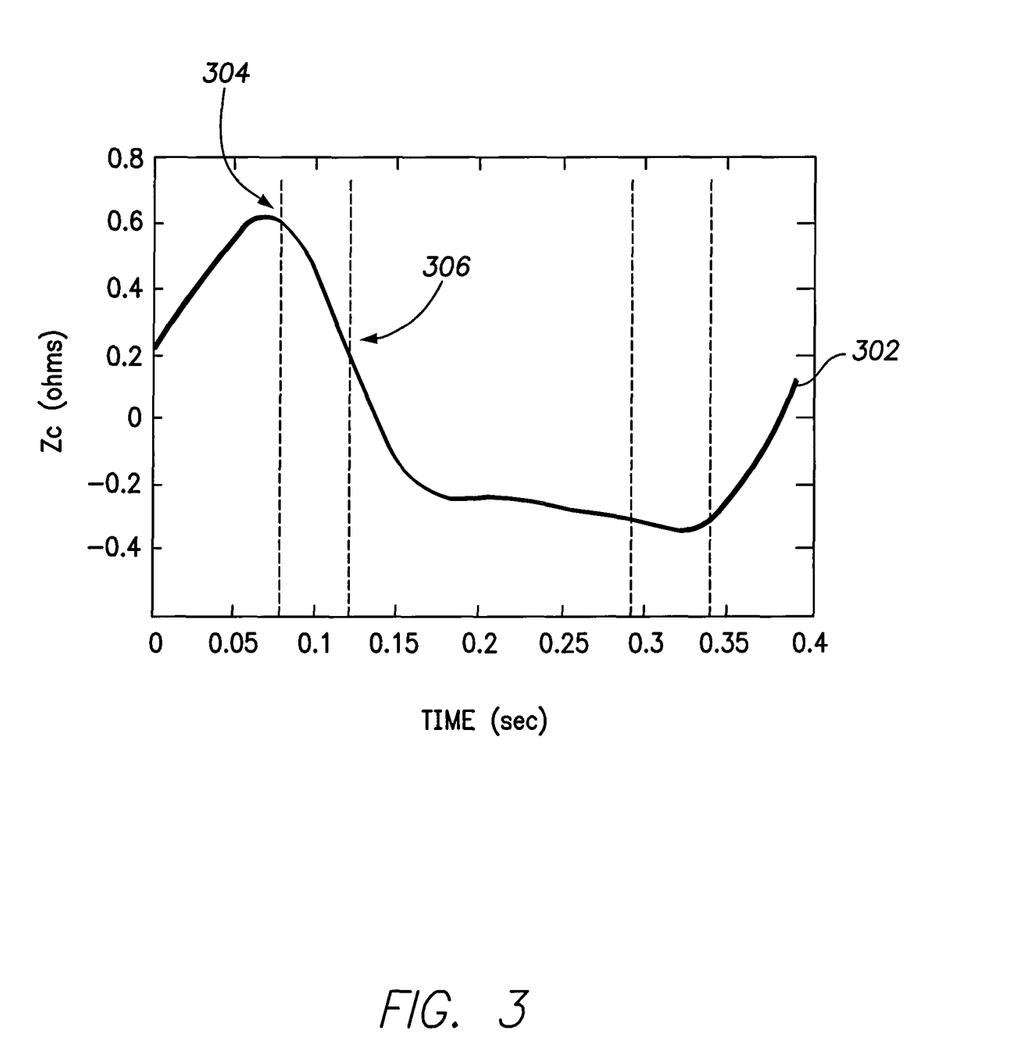
FIG. 3 illustrates graphs that exemplify the use of morphologic characteristics to estimate a timing of a mechanical function landmark.

FIG. 3 shows an example of DI morphology having characteristics that are used to estimate an MF landmark. The DI morphology 302 represents DI data collected along an RA-CAN vector where the 0 ms time coincides with the peak of the P-wave and the V pace marker. One morphologic characteristic is the peak value of the DI morphology, which indicates the point in time when the MVC. The point 304 represents the peak value of the DI morphology 302. Another morphologic characteristic is a select (e.g., maximum) negative value of the derivative (or slope) of the DI morphology, which indicates the point in time when the aortic valve opens. Time marker 306 represents the time at which the aortic valve opens for the DI morphology 302.

Returning to FIG. 2, at 210, the method analyzes a first timing delay between the IACT and the MF landmark. For example, the analyzing operation may determine, as the timing delay, an interval between a reference point in time in the IACT and the MF landmark. For example, the timing delay may represent the interval between a FOI in the P-wave and the MF landmark. The timing delay may represent the time elapsed between the end of the IACT and the occurrence of the MF landmark. When the MF landmark corresponds to MV closure, the timing delay may represent the time interval or duration between the end of the P-wave and the time when the mitral valve closes. As another option, the timing delay may represent the time interval or duration between the start of the P-wave and the time when the mitral valve closes. Optionally, the timing delay may represent the time interval or duration between the peak of the P-wave and the time when the mitral valve closes. As another option, the timing delay may represent the time interval or duration between the time when the P-wave falls below a threshold (e.g., 30% of the peak value) and when the aortic valve opens. As another option, the timing delay may represent the time interval or duration between the time when the P-wave reaches a threshold (e.g., 30% of the peak value) and when the mitral valve closes.

Optionally, at 210, the method may analyze a second timing delay. The second timing delay provides an estimate of the electrical-mechanical delay that may be useful to monitor HF. For example, the second timing delay may be determined by calculating the time interval or duration between the peak of the QRS complex and the point in time when the MF landmark occurs as determined at 208 (e.g., estimate when the mitral valve closes or when the aortic valve opens). Optionally, the time delay may calculate the interval or duration between the end of the IACT and the time when the MF landmark occurs. For example, the second timing delay may be the time interval or duration between the end of the IACT, determined by end of the P-wave as sensed by an electrode in the LV, and the closure of the mitral valve.

At 212, the method determines whether the first timing delay is greater than a timing delay threshold (TDT). The TDT represents a critical value that is determined by a clinician or technician prior to implementation of the method. As an example, the TDT may be approximately 20 ms. A first timing delay that is less than the TDT may indicate reversal of the E/A ratio. The E/A ratio may indicate ventricular filling velocities. As such, when flow across the mitral valve is assessed with pulse-wave (PW) Doppler echocardiography, two waves are characteristically seen. These represent passive filling of the ventricle (e.g., an E-wave) and active filling (e.g., an A-wave) with atrial systole. Normally, the velocity of the E-wave is greater than the velocity of the A-wave. When the first timing delay is less than the TDT, this may indicate reversal of the E/A ratio (e.g., the velocity of the A-wave is greater than the velocity of the E-wave), which may indicate diastolic dysfunction.

If the first timing delay is less than the TDT, the flow moves to 214. Otherwise, the flow moves to 216.

Optionally, at 212, the method may determine whether the second delay is greater than a heart failure monitor threshold (HFMT). The HFMT also represents a critical value that is predetermined by a clinician or technician. For example, the HFMT may be in the range of 20-60 ms. A second timing delay that is less than the HFMT may indicate HF. If the second timing delay is less than the HFMT, the flow moves to process 214. Otherwise, the flow moves to 216.

At 214, the method adjusts a therapy parameter, based on either the first or the second timing delay. For example, the method may add 20 ms to the existing AV delay to determine a new AV delay. The method may then repeat processes 202-214 with the new AV delay and reevaluate the results of the timing delay analysis. The processes 202-214 may be repeated while adjusting the AV delay during each iteration until satisfactory therapy parameters are established.

At 216, the method identifies the new IMD therapy configuration that yields desired cardiac function, as indicated by the timing delay analysis. Subsequently, based on one or more of the parameters, optionally in conjunction with other information, a clinician or the device may select a configuration (e.g., AV or VV delay, etc.) that yields the best value for the parameters.

Figure 4:
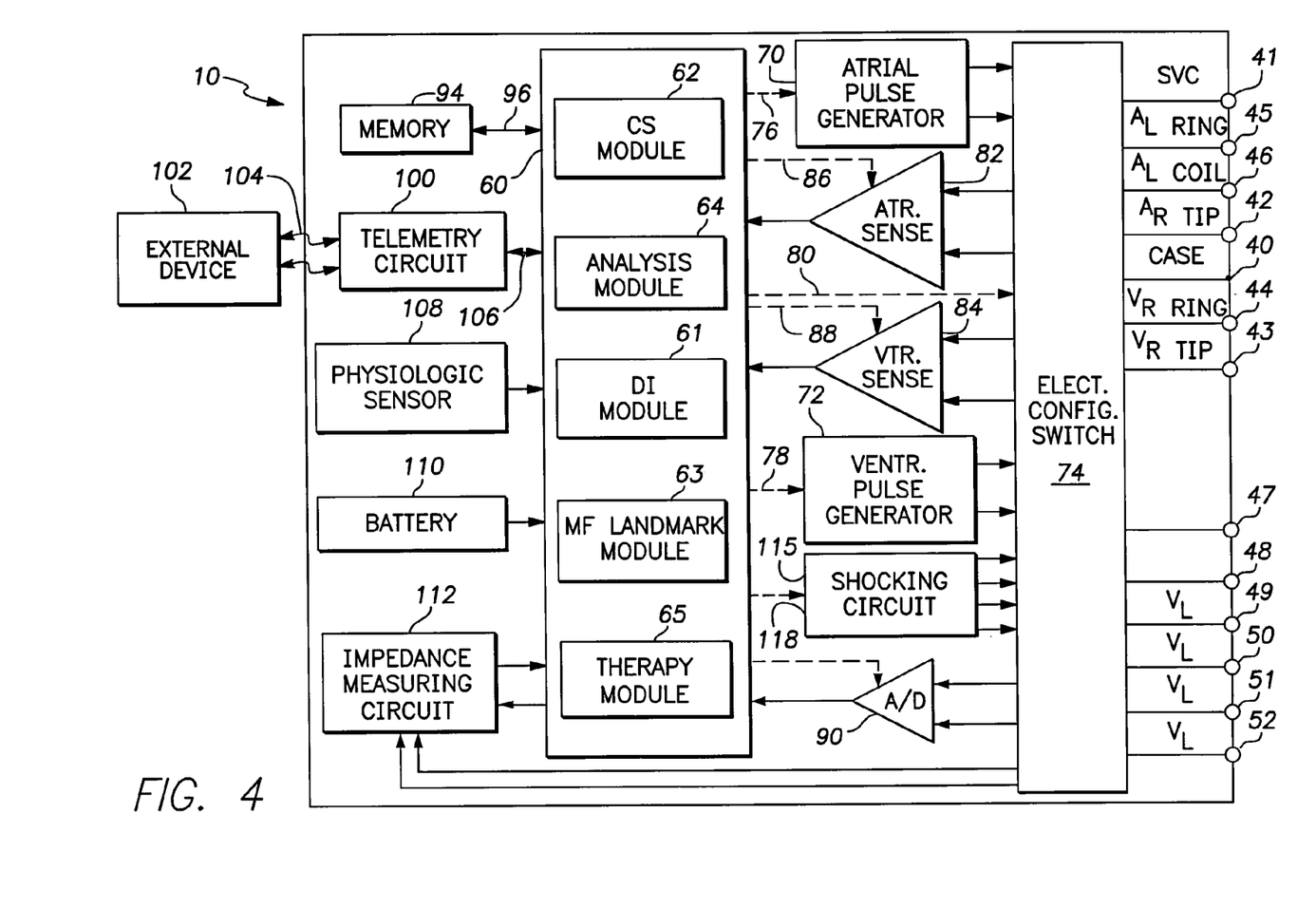
FIG. 4 illustrates a block diagram of an IMD configured to implement the methods described herein to analyze valve related timing and monitor heart failure.

FIG. 4 illustrates a block diagram of the IMD 10, which is capable of treating one or both of fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 40 for the stimulation IMD 10 is often referred to as the "can", "case" or "case electrode" and may be programmably selected to act as the return electrode for some or all sensing modes. The housing 40 may further be used as a return electrode alone or in combination with one or more of the electrodes of FIG. 1 for shocking purposes. The housing 40 further includes a connector (not shown) having a plurality of terminals 41-52. To achieve sensing, pacing and shocking in desired chambers of the heart, the terminals 41-52 are selectively connected to corresponding combinations of electrodes 22-38.

The IMD 10 includes a programmable microcontroller 60 that controls the various modes of sensing and stimulation therapy. The microcontroller 60 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 60 includes the ability to process or monitor input signals (data) as controlled by a program code stored in memory. The details of the design and operation of the microcontroller 60 are not critical to the present invention. Rather, any suitable microcontroller 60 may be used.

The microcontroller 60 includes inputs that are configured to collect cardiac signals associated with electrical or mechanical behavior of a heart over at least one cardiac cycle. The cardiac signals may be IEGM signals from the atrial or ventricular sensing circuits 82 and 84 that are representative of electrical behavior of the heart. Optionally, the cardiac signals may be the output of the data acquisition system 90 that are representative of electrical behavior of the heart. The cardiac signals may be the output of the physiologic sensor 108 that are representative of mechanical behavior. As one example, the inputs are configured to collect the DI data utilizing an IMD case electrode and at least one of an SVC electrode, an IVC electrode and an RA electrode to define the AFF vector.

The microcontroller 60 includes a dynamic impedance (DI) module 61, a cardiac signal (CS) module 62, an MF landmark module 63, an analysis module 64, and a therapy module 65 (among other things).

A dynamic impedance (DI) module 61 is configured to collect dynamic impedance data along an atria-function focused (AFF) vector to form a DI data set. The DI data set includes information corresponding to the mechanical function (MF) of a valve associated with the atrial chamber of interest. The DI module 61 may collect DI data based on a select activity state and a select patient posture.

The CS module 62 is configured to identify, from the cardiac signals, the intra-atrial conduction timing (IACT) associated with the atrial chamber of interest. The CS module 62 may be further configured to identify a feature of interest (FOI) in a P-wave representing an end of the IACT.

The MF landmark 63 module is configured to estimate the MF landmark at which the mechanical function of the valve occurs based on the DI data set. Furthermore, the MF module 63 may be configured to estimate the MF landmark by determining a timing of an impedance waveform peak associated with the DI data set. The MF landmark module 63 may be further configured to estimate one of the mitral valve closure or mitral valve opening in the right atrium. The MF landmark module 63 may still be further configured to determine, as a morphologic characteristic, at least one of i) a peak, or ii) a maximum negative change per unit time (dZ/dt) of the DI data.

The analysis module 64 is configured to analyze a timing delay between the MF landmark and the IACT. The analysis module 64 may be further configured to analyze at least one morphologic characteristic of the DI data set to estimate the MF landmark. The analysis module 64 may be further configured to identify a second timing delay between a peak of a QRS complex from the cardiac signals and the MF landmark, wherein the MF landmark represents opening of an aortic valve, and utilizing the timing delay to monitor progression of heart failure. The analysis module 64 may be further configured to determine, from a P-wave, a time between right atrial and left atrial activation, in a single cycle, the total duration constituting the IACT. The analysis module 64 may be further configured to monitor the timing delay for progression of heart failure. The analysis module 64 may be further configured to determine, as the time delay, an interval between the FOI in the P-wave and the MF landmark.

The therapy module 65 is configured to modulate, over multiple cardiac cycles, at least one therapy parameter while the IMD 10 obtains a collection of at least one AFF indicators associated with different therapy parameters. The therapy module 65 may adjust, based on timing delay, a therapy to encourage atrial contribution to ventricular filling.

The memory 94 stores correlation metrics associated with the cardiac functions of interest, such as CSF-DI correlation metrics. The memory 94 also stores the CSF indicators, DI data, cardiac signals, and associated IMD therapy parameter values for each iteration through the methods of FIG. 1B.

An atrial pulse generator 70 and a ventricular pulse generator 72 generate pacing and ATP stimulation pulses for delivery by desired electrodes. The electrode configuration switch 74 (also referred to as switch bank 74) controls which terminals 41-52 receive shocks or pacing pulses. The atrial and ventricular pulse generators, 70 and 72, may include dedicated, independent pulse generators, multiplexed pulse generators, shared pulse generators or a single common pulse generator. The pulse generators 70 and 72 are controlled by the microcontroller 60 via appropriate control signals 76 and 78, respectively, to trigger or inhibit stimulation pulses. The microcontroller 60 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 74 connects the sensing electronics to the desired terminals 41-52 of corresponding sensing electrodes 22-38. For example, terminals 49-52 may be coupled to LV electrodes 23-26. The switch 74 may connect terminals 41-52 to one or more ventricular sensing circuits 84, which provide cardiac signals, representative of cardiac activity, to the microcontroller. The circuit 84 may amplify, filter, digitize and/or otherwise process the sensed cardiac signals from the LV electrodes 23-26. The circuit 84 may provide separate, combined or difference signals to the microcontroller 60 representative of the sensed signals from the LV electrodes 23-26. The circuit 84 may also receive sensed signals from the RV tip electrode 32 and the RV ring electrode 34 through terminals 43 and 44, respectively. The atrial sensing circuit 82 is connected through the switch 74 to terminals 42 and 45-46 to desired RA and/or LA electrodes 22 and 27-28 to sense RA and/or LA cardiac activity. The switch 74 also connects various combinations of the electrodes 22-38 to an impedance measuring circuit 112.

An impedance measuring circuit 112 collects multiple measured impedances between corresponding multiple combinations of electrodes 22-38. For example, the impedance measuring circuit 112 may collect a measured impedance for each or a subset of the active sensing vectors 151-155. Optionally, the impedance measuring circuit 112 may also monitor lead impedance during the acute and chronic phases for proper lead positioning or dislodgement; detects operable electrodes and automatically switches to an operable pair if dislodgement occurs; measures respiration or minute ventilation; measures thoracic impedance for determining shock thresholds; detects when the device has been implanted; measures stroke volume; and detects the opening of heart valves, etc.

The switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, co-bipolar, etc.) by selectively closing the appropriate combination of switches (not specifically shown). Atrial sensing circuits 82 and ventricular sensing circuits 84 may also be selectively coupled to the right atrial lead 20, LV lead 21, and the RV lead 30, through the switch 74 for detecting the presence of cardiac activity in each of the four chambers of the heart. The switch 74 determines the "sensing polarity" of the cardiac signal by selectively closing the appropriate switches.

The outputs of the atrial and ventricular sensing circuits 82 and 84 are connected to the microcontroller 60 which, in turn, is able to trigger or inhibit the atrial and ventricular pulse generators 70 and 72, respectively. The sensing circuits 82 and 84, in turn, receive control signals over signal lines 86 and 88 from the microcontroller 60 for purposes of controlling the gain, threshold, the polarization charge removal circuitry (not shown), and the timing of any blocking circuitry (not shown) coupled to the inputs of the sensing circuits, 82 and 86.

Cardiac signals are also applied to the inputs of an analog-to-digital (A/D) data acquisition system 90. The data acquisition system 90 is configured to acquire intra-cardiac electrogram signals, convert the raw analog data into a digital signal, and store the digital signals for later processing and/or telemetric transmission to an external IMD 102. The data acquisition system 90 samples cardiac signals across any pair of desired electrodes. The data acquisition system 90 may be coupled to the microcontroller 60, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 60 is further coupled to a memory 94 by a suitable data/address bus 96. The memory 94 stores programmable operating, impedance measurements, impedance derivation and therapy-related parameters used by the microcontroller 60. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart 12 within each respective tier of therapy.

The impedance derivation parameters may include information designating i) sensing electrodes to use to define active sensing vectors, ii) sets and subsets of sensing vectors to use to monitor various regions of the heart, iii) sets or subsets of active sensing vectors to combine to form each pseudo sensing vector, iv) weight valves to use with active sensing vectors to form each pseudo sensing vector, v) algorithms for how to mathematically combine active sensing vectors to form each pseudo sensing vector, and the like.

The operating and therapy-related parameters may be non-invasively programmed into the memory 94 through a telemetry circuit 100 in telemetric communication with the external IMD 102, such as a programmer, trans-telephonic transceiver, or a diagnostic system analyzer. The telemetry circuit 100 is activated by the microcontroller 60 by a control signal 106. The telemetry circuit 100 advantageously allows intra-cardiac electrograms and status information relating to the operation of the IMD 10 (as contained in the microcontroller 60 or memory 94) to be sent to the external IMD 102 through an established communication link 104.

The stimulation IMD 10 may include a physiologic sensor 108 to adjust pacing stimulation rate according to the exercise state of the patient. The physiological sensor 108 may further be used to detect changes in cardiac output, changes in the physiological condition of the heart, or diurnal changes in activity (e.g., detecting sleep and wake states). The battery 110 provides operating power to all of the circuits shown in FIG. 4.

The microcontroller 60 further controls a shocking circuit 116 by way of a control signal 118. The shocking circuit 116 generates stimulating pulses of low (up to 0.5 Joules), moderate (0.5-10 Joules), or high energy (11 to 40 Joules), as controlled by the microcontroller 60. Stimulating pulses are applied to the patient's heart 12 through at least two shocking electrodes, and as shown in this embodiment, selected from the left atrial (LA) coil electrode 28, the RV ring electrode 34, the SVC coil electrode 38 and/or the housing 40.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for analyzing valve-related mechanical timing, the method comprising:
    collecting cardiac signals associated with an atrial chamber of interest using an implantable medical device;
    collecting dynamic impedance (DI) data along an atria-function focused (AFF) vector to form a DI data set, the DI data set including information corresponding to a mechanical function (MF) of a valve associated with the atrial chamber of interest;
    identifying, from the cardiac signals, an intra-atrial conduction timing (IACT) associated with the atrial chamber of interest;
    estimating an MF landmark at which the mechanical function of the valve occurs based on the DI data set;
    analyzing a timing delay between the MF landmark and the IACT;
    adjusting a therapy, based on the timing delay, to encourage atrial contribution to ventricular filling; and
    applying the adjusted therapy to one or more chambers of the heart using the implantable medical device.

2. The method of claim 1, wherein the identifying includes identifying a feature of interest (FOI) in a P-wave representing an end of the IACT, the analyzing operation further comprising determining, as the time delay, an interval between the FOI in the P-wave and the MF landmark.

3. The method of claim 1, wherein the estimating operation includes estimating the MF landmark by determining a timing of an impedance waveform peak associated with the DI data set.

4. The method of claim 1, wherein the first chamber represents the right atrium and the MF landmark represents an estimate for one of mitral valve closure (MVC) or mitral valve opening (MVO).

5. The method of claim 1, wherein the analyzing comprises analyzing at least one morphologic characteristic of the DI data set to estimate the MF landmark.

6. The method of claim 1, further comprising identifying a second timing delay between a peak of a QRS complex from the cardiac signals and the MF landmark, wherein the MF landmark represents opening of an aortic valve, and utilizing the timing delay to monitor progression of heart failure.

7. The method of claim 1, wherein the identifying includes determining, from a P-wave, a time between right atrial and left atrial activation, in a single cycle, the total duration constituting the IACT.

8. The method of claim 1, further comprising monitoring the timing delay for progression of heart failure.

9. The method of claim 1, wherein the collecting of DI data includes utilizing an IMD case electrode and at least one of an SVC electrode and an RA electrode to define the AFF vector and to collect the DI data.

10. The method of claim 1, wherein the estimating the MF landmark includes determining, as a morphologic characteristic, at least one of i) a peak, or ii) a maximum negative change per unit time (dZ/dt) of the DI data.

11. A system for characterizing analyzing valve-related mechanical timing, comprising:
    inputs configured to collect cardiac signals associated with an atrial chamber of interest; and
    a processor configured to:
        collect dynamic impedance data along an atria-function focused (AFF) vector to form a DI data set, the DI data set including information corresponding to a mechanical function (MF) of a valve associated with the atrial chamber of interest;
        identify, from the cardiac signals, an intra-atrial conduction timing (IACT) associated with the atrial chamber of interest;
        estimate an MF landmark at which the mechanical function of the valve occurs based on the DI data set;
        analyze a timing delay between the MF landmark and the IACT; and
        adjust a therapy, based on the timing delay, to encourage atrial contribution to ventricular filling.

12. The system of claim 11, wherein the processor is further configured to identify a feature of interest (FOI) in a P-wave representing an end of the IACT, and to determine, as the time delay, an interval between the FOI in the P-wave and the MF landmark.

13. The system of claim 11, wherein the processor is further configured to estimate the MF landmark by determining a timing of an impedance waveform peak associated with the DI data set.

14. The system of claim 11, wherein the processor is further configured to estimate for one of mitral valve closure (MVC) or mitral valve opening (MVO) in the right atrium.

15. The system of claim 11, wherein the processor is further configured to analyze at least one morphologic characteristic of the DI data set to estimate the MF landmark.

16. The system of claim 11, wherein the processor is further configured to identify a second timing delay between a peak of a QRS complex from the cardiac signals and the MF landmark, wherein the MF landmark represents opening of an aortic valve, and utilizing the timing delay to monitor progression of heart failure.

17. The system of claim 11, wherein the processor is further configured to determine, from a P-wave, a time between right atrial and left atrial activation, in a single cycle, the total duration constituting the IACT.

18. The system of claim 11, wherein the processor is further configured to monitor the timing delay for progression of heart failure.

19. The system of claim 11, wherein the inputs are configured to collect DI data includes utilizing an IMD case electrode and at least one of an SVC electrode and an RA electrode to define the AFF vector and to collect the DI data.

20. The system of claim 11, wherein the processor is further configured to determine, as a morphologic characteristic, at least one of i) a peak, or ii) a maximum negative change per unit time (dZ/dt) of the DI data.

* * * * *